US012730112B2

(12) United States Patent
Covey et al.

(10) Patent No.: US 12,730,112 B2
(45) Date of Patent: Sep. 8, 2026

(54) SOLID-PHASE AFFINITY SELECTION BY MASS SPECTROMETRY

(71) Applicant: DH TECHNOLOGIES DEVELOPMENT PTE. LTD., Singapore (SG)

(72) Inventors: Thomas R. Covey, Concord (CA); Chang Liu, Concord (CA)

(73) Assignee: DH Technologies Development Pte. Ltd., Singapore (SG)

( * ) Notice: Subject to any disclaimer, the term of this patent is extended or adjusted under 35 U.S.C. 154(b) by 795 days.

(21) Appl. No.: 17/999,621

(22) PCT Filed: May 20, 2021

(86) PCT No.: PCT/IB2021/054397

§ 371 (c)(1),
(2) Date: Nov. 22, 2022

(87) PCT Pub. No.: WO2021/234640

PCT Pub. Date: Nov. 25, 2021

(65) Prior Publication Data

US 2023/0236201 A1 Jul. 27, 2023

Related U.S. Application Data

(60) Provisional application No. 63/029,028, filed on May 22, 2020.

(51) Int. Cl.
*G01N 33/68* (2006.01)
*G01N 27/624* (2021.01)
(Continued)

(52) U.S. Cl.
CPC ....... *G01N 33/6851* (2013.01); *G01N 27/624* (2013.01); *G01N 27/745* (2013.01); *G01N 33/54326* (2013.01)

(58) Field of Classification Search
CPC .............. G01N 27/624; G01N 27/745; G01N 33/54326; G01N 33/6848; G01N 33/6851
See application file for complete search history.

(56) References Cited

U.S. PATENT DOCUMENTS

| | | |
|---|---|---|
| 5,582,665 A | 12/1996 | Eigen et al. |
| 6,649,419 B1 | 11/2003 | Anderson |

(Continued)

FOREIGN PATENT DOCUMENTS

| | | |
|---|---|---|
| CN | 101019026 A | 8/2007 |
| CN | 101842161 A | 9/2010 |

(Continued)

OTHER PUBLICATIONS

PCT International Search Report and Written Opinion in International Application PCT/IS2021/054397, mailed Sep. 22, 2021, 11 pages.

(Continued)

*Primary Examiner* — Jennifer Wecker
(74) *Attorney, Agent, or Firm* — Merchant & Gould P.C.

(57) ABSTRACT

In a system for affinity selection by mass spectrometry, wherein a plurality of drug candidates in solution are separated based on affinity, a method is provided comprising introducing a solid-phase device having binding affinity for a selected protein into the solution, binding at least one of the plurality of drug candidates to the solid-phase device as a selected drug candidate, washing the solid-phase device and selected drug candidate to separate unbound material, sampling the selected drug candidate in capture fluid flowing
(Continued)

through a sampling region of an open port sampling interface and directing the sampled selected drug candidate and capture fluid to an ionization source.

20 Claims, 8 Drawing Sheets

(51) Int. Cl.
*G01N 27/74* (2006.01)
*G01N 33/543* (2006.01)

(56) References Cited

U.S. PATENT DOCUMENTS

| | | | |
|---|---|---|---|
| 7,923,681 | B2 | 4/2011 | Collings et al. |
| 8,585,279 | B2 | 11/2013 | Rida |
| 10,103,015 | B2 | 10/2018 | Arnold et al. |
| 10,656,147 | B2 | 5/2020 | Campbell et al. |
| 2003/0134416 | A1 | 7/2003 | Yamanishi et al. |
| 2004/0229346 | A1 | 11/2004 | Kohara et al. |
| 2005/0287577 | A1 | 12/2005 | Yamamichi |
| 2008/0150521 | A1 | 6/2008 | Meeten |
| 2008/0217254 | A1 | 9/2008 | Anderson |
| 2009/0053689 | A1 | 2/2009 | Oviso, Jr. |
| 2013/0027686 | A1 | 1/2013 | Balluch et al. |
| 2013/0143324 | A1 | 6/2013 | Aleksandrova et al. |
| 2013/0337455 | A1 | 12/2013 | McNaughton et al. |
| 2017/0246625 | A1 | 8/2017 | Becker et al. |
| 2017/0316926 | A1 | 11/2017 | Arnold et al. |
| 2018/0369831 | A1 | 12/2018 | Arnold et al. |
| 2019/0346435 | A1 | 11/2019 | Yanik et al. |
| 2020/0043712 | A1 | 2/2020 | Arnold et al. |
| 2020/0360879 | A1 | 11/2020 | Arnold et al. |
| 2020/0365382 | A1 | 11/2020 | Arnold et al. |
| 2022/0088601 | A1 | 3/2022 | Orion et al. |
| 2023/0096792 | A1 | 3/2023 | Arnold |
| 2023/0405594 | A1 | 12/2023 | Liu |
| 2024/0053356 | A1 | 2/2024 | Liu |
| 2024/0255473 | A1 | 8/2024 | Covey |
| 2025/0296089 | A1 | 9/2025 | Faur |
| 2025/0303403 | A1 | 10/2025 | Patel |

FOREIGN PATENT DOCUMENTS

| | | | | |
|---|---|---|---|---|
| CN | 109073518 A | 12/2018 | | |
| EP | 2015074 A1 | 1/2009 | | |
| EP | 2440941 | 4/2012 | | |
| EP | 2581746 | 4/2013 | | |
| WO | 00/25922 | 5/2000 | | |
| WO | 02/090565 | 11/2002 | | |
| WO | 2004/004874 | 1/2004 | | |
| WO | 2015/128725 | 9/2015 | | |
| WO | 2016/063389 | 4/2016 | | |
| WO | WO-2016118489 A1 * | 7/2016 | ............ | G01N 33/78 |
| WO | 2017/093896 | 6/2017 | | |
| WO | 2018/138631 | 8/2018 | | |
| WO | 2018/217778 | 11/2018 | | |
| WO | 2019/102355 | 11/2018 | | |
| WO | 2019/126363 | 6/2019 | | |
| WO | 2019/234708 | 12/2019 | | |
| WO | 2020/003233 | 1/2020 | | |
| WO | 2020/079647 A1 | 4/2020 | | |
| WO | 2021/203005 | 10/2021 | | |
| WO | 2021/234640 | 11/2021 | | |
| WO | 2023/121990 | 6/2023 | | |

OTHER PUBLICATIONS

PCT International Preliminary Report on Patentability in International Application PCT/IS2021/054397, mailed Dec. 1, 2022, 9 pages.

Liu Chang et al., "Fast quantitation of opioid isomers in human plasma by differential mobility spectrometry/mass spectrometry via SPME/open-port probe sampling interface", Analytica Chimica Acta, vol. 991, Aug. 28, 2017, pp. 89-94.

Zhang Hui et al., "Acoustic Ejection Mass Spectrometry for High-Throughput Analysis", bioRxiv, Jan. 29, 2020, retrieved from internet on Sep. 8, 2021 at: https://www.biorxiv.org/content/10.1101/2020.01.28.923938v1.full.pdf.

Ghislain Luke et al., "A new platform for high-throughput mass spectometry: acoustic droplet ejection with an open port probe sampling interface", Rapid Communications in Mass Spectrometry, Jan. 1, 2018, pp. 1749-1756.

Choi, Yongsoo et al., "Development of a Screening Assay for Ligands to the Estrogen Receptor Based on Magnetic Microparticles and LC-MS", Combinatorial Chemistry and High Throughput Screening, vol. 11, No. 1, Jan. 1, 2008, pp. 106.

Hager et al., "Product Ion Scanning Using a Q-q-Qlinear ion trap (QTRAP) Mass Spectrometer", Rapid Communications in Mass Spectrometry, 2003; 17: 1056-1064.

Jegatha Nambi Krishnan et al., "Rapid microfluidic separation of magnetic beads through dielectrophoresis and magnetophoresis", Electrophoresis, Verlag Chemis, Hoboken, NJ, vol. 30, No. 9, May 7, 2009, pp. 1457-1463.

Johnson, Benjamin et al., "Applications of Pulsed Ultrafiltration-Mass Spectrometry", Mass Spectrometry Reviews, 2002, 21, pp. 76-86.

Jonker, Niels et al., "Direct Dynamic Protein-Affinity Selection Mass Spectrometry", Chromatographia, Jul. 2010; 72 (No. 1-2): 7-13.

Moein et al., "Solid Phase Microextraction and Related Techniques for Drugs in Biological Samples", J. Anal. Methods Chem. 2014, published Feb. 13, 2014; 25 pgs.

O'Connell et al., Solution-Based Indirect Affinity Selection Mass Spectrometry—A General Tool for High-Throughput Screening of Pharmaceutical Compound Libraries, Anal. Chem., 2014, 86, pp. 7413-7420.

Rasolzadeh, Fahimeh et al., "Magnetic fiber headspace solid-phase microextraction coupled to GC-MS for the extraction and quantitation of polycyclic aromatic hydrocarbons", Mikrochimica Acta, Springer Verlag, Vienna, AT, vol. 186, No. 7, Jun. 13, 2019, pp. 1-9.

Rush, Michael et al., "Development of a Magnetic Microbead Affinity Selection Screen (MagMASS) Using Mass Spectrometry for Ligands to the Retinoid X Receptor-[alpha]", Journal of the American Society for Mass Spectrometry, Elsevier, vol. 28, No. 3, Dec. 13, 2016, pp. 479-485.

Rush, Michael et al., "Magnetic Microbead Affinity Selection Screening (MagMASS) of Botanical Extracts for Inhibitors of 15-Lipoxygenase", Journal of Natural Products, vol. 79, No. 11, Nov. 1, 2016, pp. 2898-2902.

van Breemen, Richard et al., "Pulsed Ultrafiltration Mass Spectrometry: A New Method for Screening Combinatorial Libraries", Anal. Chem., 1997, 69, pp. 2159-2164.

Zhang, Bingjie et al., "A Novel G Proten-Based and Subject-Selective Agonist for a G Protein-Coupled Receptor Discovered for Screening Herbal Extracts", ACS Central Science, vol. 6, No. 2, Jan. 23, 2020, pp. 213-225.

* cited by examiner

SOLID-PHASE AFFINITY SELECTION BY MASS SPECTROMETRY

CROSS-REFERENCE TO RELATED CASES

This application is a National Stage Application of PCT International Patent Application No. PCT/IB2021/054397, filed on May 20, 2021, which claims the benefit of priority to U.S. Provisional Application No. 63/029,028, filed on May 22, 2020, the contents of which are incorporated herein by reference in their entireties. To the extent appropriate, a claim of priority is made to each of the above disclosed applications.

FIELD

The present invention is directed to processing fluids, and more particularly, to methods and systems for identifying and separating compounds based on a selected affinity.

BACKGROUND

Affinity selection by mass spectrometry (ASMS) involves the binding of candidate molecules to immobilized or soluble receptors and has been used for screening large compound libraries in a time and cost-effective manner. The conventional ASMS workflow is based on solution phase incubation, wherein a target protein in solution is added to a mixture of the drug molecules. The unbounded drug molecules are then separated from the drug-protein complex by mechanisms such as ultrafiltration, spin-column, and size-exclusion chromatography. After separation based on molecular weight, the protein-drug complex and the unbounded protein are injected to a reverse-phase LC/MS for analysis. The drug molecules detected by MS (released in LC) are identified with the binding affinity to the target protein. However, the analysis speed according to convention methodologies is limited due to time-consuming separation (i.e. elution) of free drugs from the protein-drug complex using LC.

In solid phase ASMS, an enzyme on the surfaces of solid phase devices may be inserted into a drug mixture in solution to capture drug molecules with affinity to the solid phase surfaces of the solid phase devices. Examples of such solid phase devices include magnetic particles and Solid Phase MicroExtraction (SPME) fibers, however in comparison with other solid-phase devices like SPME fibers, magnetic particles have much more surface area, which improves capture sensitivity. In one such approach, MagMASS (*J. Nat. Prod.* 2016, 79, 2898-2902), magnetic particles are used to "fish-out" the drug molecules with the protein binding affinity, while leaving the un-bounded drugs in the solution. If necessary, the magnetic particles can be washed before elution of the drug molecules to the liquid phase and ejection to LC-MS/MS.

It is also known to use an open-port sampling interface (OPI) for direct sampling of solid phase substrates with bounded drug molecules, such as SPME fibers (see U.S. Pat. No. 10,103,015B2, the contents of which are incorporated herein by reference), and where the solid phase devices are magnetic particles to use a magnet (e.g. electromagnet) for transfer of magnetic particles between sample wells and/or from a sample well to the OPI (see PCT/IB2018/089146, the contents of which are incorporated herein by reference). Care must be taken when using an OPI to transfer the magnetic particles to a MS port to avoid the magnetic particles being ingested into the MS.

The following references are relevant as background: Solid Phase Microextraction and Related Techniques for Drugs in Biological Samples by Moen et al., *J. Anal. Methods Chem.* 2014, published Feb. 13, 2014; Direct Dynamic Protein-Affinity Selection Mass-Spectrometry by Niels Jonker et al., *Chromatographia,* 2010 July; 72(1-2): 7-13; Solution-Based Indirect Affinity Selection Mass Spectrometry—A General Tool for High-Throughput Screening of Pharmaceutical Compound Libraries by O'Connell et al., *Anal. Chem.,* 2014, 96, pp. 7413-7420; Pulsed Ultrafiltration Mass Spectrometry: A New Method for Screening Combinatorial Libraries by Richard B. van Breemen et al., *Anal. Chem.,* 1997, 69, pp. 2159-2164; Magnetic Microbead Affinity Selection Screening (MagMASS) of Botanical Extracts for Inhibitors of 15-Lipoxygenase by Michael D Rush, et al., *J. Nat. Prod.* 2016, 79, pp. 2898-2902; APPLICATIONS OF PULSED ULTRAFILTRATION-MASSSPECTROMETRY by Benjamin M. Johnson, *Mass Spectrometry Reviews,* 2002, 21, pp. 76-86; WO2017/093896 AI (Don W. Arnold, et al.) and WO2019/102355 AI (Don W. Arnold, et al.)

SUMMARY

It is an aspect of the present invention to provide an improved method and apparatus for transferring candidate molecules into an open port sampling interface OPI.

In one aspect, candidate molecules are isolated from solid phase devices in a preparation stage (sample well(s)) and then introduced (without the solid phase devices) into the OPI using a process that does not require the sample to be aspirated off using suction.

In another aspect, candidate molecules, bound or unbound, are introduced into the OPI according to a process that filters out the solid phase devices before introduction of ions into the MS. In one embodiment, preparation steps are conducted in the sample well(s) and then the isolated and solid phase devices are ejected into the OPI where the sample is separated from the solid phase devices using a solvent-based capture fluid. The solid phase devices are then trapped before entering the MS. In an embodiment, an a external magnetic field to trap the solid phase devices before delivering the sample to the MS ion source. In another embodiment, a trap may be provided before the electrospray ionization the OPI or in-line with the transfer conduit.

In yet a further aspect, a number of the preparation steps may be performed in the OPI and transfer conduit, with fewer steps being performed in the sample well(s). For example, a first capture fluid may be used to capture the sample and solid phase devices that provides a washing action as the solid phase devices are trapped with sample, and a second separation fluid (i.e. a solvent) may then be used to separate the sample from the trapped solid phase devices. In an embodiment, the second separation fluid may flow with a varying concentration gradient where the concentration increases from 0-100% according to a pre-defined ramp or sequence of concentration increases. Also, in an embodiment a MS signal may be used to trigger switching from the first capture fluid to the second separation fluid. In this embodiment, the first capture fluid is directed to the MS, which is useful if the wash components are MS compatible. In another embodiment the capture fluid may be directed to a waste conduit and a timer may be used to trigger switching from the first capture fluid to the second separation fluid and to direct the separation fluid to the ion source, which is useful if the wash components are not MS compatible.

Also, according to aspects set forth herein, an OPI may be used to simplify the use of magnetic beads in solid phase ASMS. According to other aspects, the solid-phase device need not be magnetic, and the drug molecule candidate may be isolated based on size.

In other aspects the solid-phase device may be uniformly suspended in the solution, may be operative to capture a selected candidate, may be acoustically ejected from the solution with the candidate, captured in capture fluid flowing through an OPI, and may be trapped from the capture fluid by a magnetic trap to allow the candidate to flow to an MS ionization source. In some aspects, the trap may comprise a magnetic trap or a size-based trap.

The above aspects can be attained by a method for identifying and separating compounds based on a selected affinity comprising introducing a plurality of compounds together in a solution; inserting a probe comprising a surface treatment operative to bind with one or more compounds based on the selected affinity; binding one or more compounds from the plurality of compounds to the probe; removing the probe and bound one or more compounds from the solution; separating the one or more compounds from the probe; capturing the separated one or more compounds with flowing solvent at an open end of an open port sampling interface; transporting the solvent and captured one or more compounds to an ionization device; and ionizing the one or more compounds.

In an embodiment, the method may further include analyzing the ionized one or more compounds in a mass spectrometer.

In an embodiment, the method may further include, after ionizing the one or more compounds but before the analyzing, separating the ionized one or more compounds based on ion mobility in a differential mobility spectrometer.

In an embodiment, the probe is selected from the group consisting of a Solid Phase MicroExtraction (SPME) fiber; a REED (as set forth in U.S. Provisional Patent Application No. 62/692,274, the contents of which are incorporated herein); and a magnetic bead.

In an embodiment, separating the one or more compounds from the probe may include inserting the probe and bound one or more compounds into an unbinding solvent in a separation vessel to unbind the one or more compounds from the probe, and injecting the unbinding solvent and unbound one or more compounds into the flowing solvent at the open end of the open port sampling interface.

In an embodiment, the injecting may include aspirating the unbinding solvent and unbound one or more compounds from the separation vessel and injecting the aspirated unbinding solvent and unbound one or more compounds into a solvent stream pumped to the ionization device.

In an embodiment, the injecting may include ejecting droplets of the unbinding solvent and unbound one or more compounds from the separation vessel into the flowing solvent at the open end of the open port sampling interface.

In an embodiment, the injecting may include acoustically or pneumatically ejecting the droplets.

Other aspects can be attained in a system for affinity selection by mass spectrometry, wherein a plurality of drug candidates in solution are separated based on affinity, by a method comprising: introducing a solid-phase device having binding affinity for a selected protein into the solution; binding at least one of the plurality of drug candidates to the solid-phase device as a selected drug candidate; washing the solid-phase device and selected drug candidate to separate unbound material; sampling the selected drug candidate in capture fluid flowing through a sampling region of an open port interface (OPI) and directing the sampled selected drug candidate and capture fluid to an ionization source.

In an embodiment, the method may further include immobilizing the protein to the surface of the solid-phase device by treating Si—OH on the surface with aminosilane reagents followed by reaction with glutaraldehyde (GA), the free-end of GA being capable of reacting with the amino groups of lysine to capture the protein, or via streptavidin-biotin interaction or histidine tag.

In an embodiment, the method may further include sampling the selected drug candidate by acoustically ejecting the selected drug candidate from a sample well into the capture fluid.

In an embodiment, the method may further include ejecting the selected drug candidate from the sample well after the washing.

In an embodiment, the method may further include, before the selected drug candidate is ejected from the sample well, releasing the selected drug candidate from the solid-phase device, isolating the selected drug candidate from the solid-phase device, and ejecting the selected drug candidate without the solid-phase device into the capture fluid.

In an embodiment, the selected drug candidate is ejected in a bound state with the solid-phase device.

In an embodiment, the selected drug candidate is unbound by the capture fluid.

In an embodiment, the selected drug candidate and solid-phase device are ejected from the sample well, and the system further comprises a trap for trapping the solid-phase device before the ionization source.

In an embodiment, the candidate drug is released from the trapped solid-phase device by introducing solvent into the capture fluid.

In an embodiment, the trap comprises a magnetic trap.

In an embodiment, the trap comprises a filter or size trap.

In some embodiments the solid-phase device is ejected with the device separate from the candidate whereas in other embodiments the solid-phase device is ejected with the device bound to the candidate.

In some embodiments the drug molecule candidate is isolated from the solid-phase device by the capture fluid whereas in other embodiments the drug molecule candidate is isolated by a release agent (e.g. solvent) after the solid-phase device is trapped from the capture fluid.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
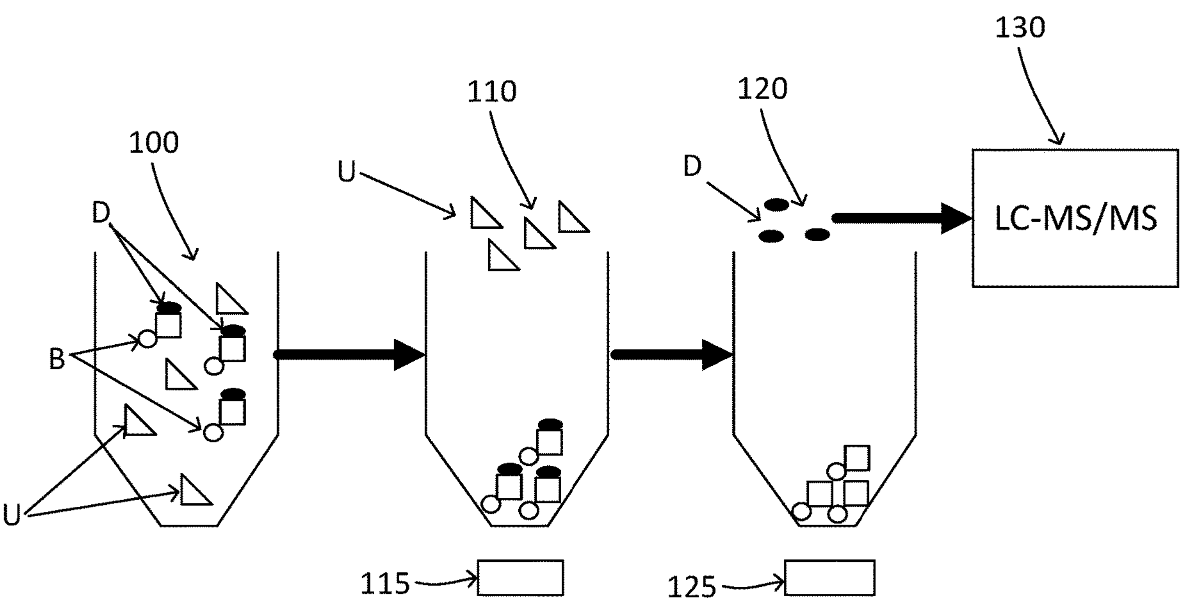
FIG. 1 shows steps in the MagMASS method of using magnetic particles are used to capture drug molecules with protein binding affinity.

The inventors have found that the prior art MagMASS method uses magnetic particles to capture drug molecules with protein binding affinity, as shown in FIG. 1. First, magnetic beads (B) are introduced to a sample vessel 100 containing drug molecule candidates (U and D) in solution. Drug molecule candidates with affinity (D) then bind to the magnetic beads. The unbound drug molecules (U) are then removed in a wash vessel 110 while the beads (B) and bound drug molecule candidate (D) are retained in the vessel via a magnetic field from magnet 115. The washed beads are removed from the wash vessel and introduced into a separation vessel 120 where the drug molecule candidate (D) is isolated from the beads using a solvent. The isolated drug molecule candidate (d) is then aspirated from the separation vessel 120 while the magnetic beads are held in place via a magnetic field from magnet 125. The aspirated drug molecule candidate is then eluted over time into a LC-MS/MS 130 for analysis. The magnetic beads can then be magnetically removed from the separation vessel 120.

As discussed above, aspects of the present invention include an improved method and apparatus for transferring candidate molecules using an OPI with magnetic beads as the solid phase device, and acoustic droplet ejection technology for non-contact introduction of samples to the OPI in a precise and controlled manner.

Figure 2:
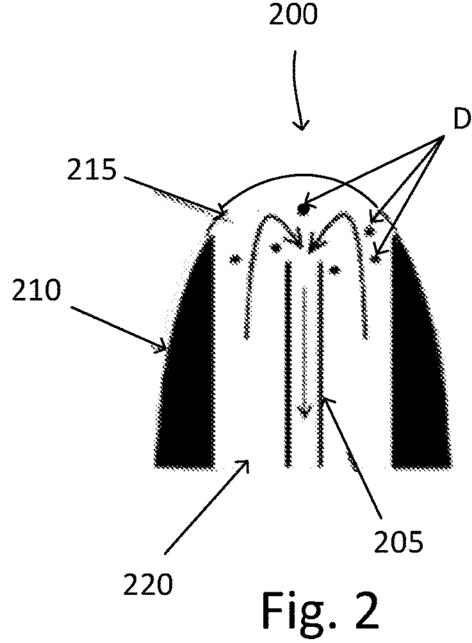
FIG. 2 is s schematic representation of an open port sampling interface (OPI) used in embodiments.

With reference to FIG. 2, an OPI 200 is shown comprising a first cylindrical member 205 disposed within a second cylindrical member 210 arranged in a co-axial arrangement, and an open-ended tip 215. Additional details of the OPI 200 are provided below with reference to various embodiments.

Figure 3:
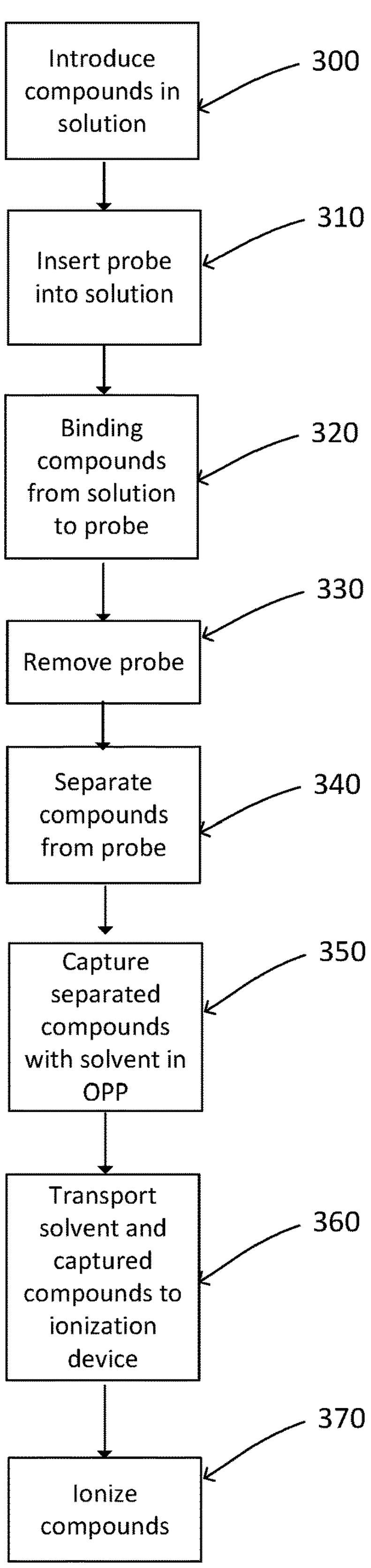
FIG. 3 depicts a method for identifying and separating compounds based on a selected affinity.

In general, a method is provided for identifying and separating compounds based on a selected affinity, as shown in FIG. 3. At 300, a plurality of compounds is introduced together in a solution. At 310, a probe is inserted into the solution, where the probe includes a surface treatment operative to bind with one or more compounds based on selected affinity. One or more of the compounds then bind to the probe at 320. In an embodiment, the substrate surface may comprise a Solid Phase Microextraction (SPME) fibre that can contain an embedded protein with binding affinity. The substrate surface may be any material configured to hold the protein and can include various examples such as a mesh material or blade like surface or REED. In other embodiments, as discussed below, the surface treatment can include magnetic material such as beads.

The probe with bound one or more compounds is then removed from the solution at 330. At 340, the one or more compounds are separated from the probe. At 350, the separated one or more compounds are captured with flowing organic solvent at the open-ended tip 215 of OPI 200. At 360, the solvent and captured one or more compounds at the open-ended tip 215 of OPI 200 are transported to an ionization device, such as LC-MS/MS 130. Then, at 370, the one or more compounds are ionized within LC-MS/MS 130, as is known in the art.

Figure 4:
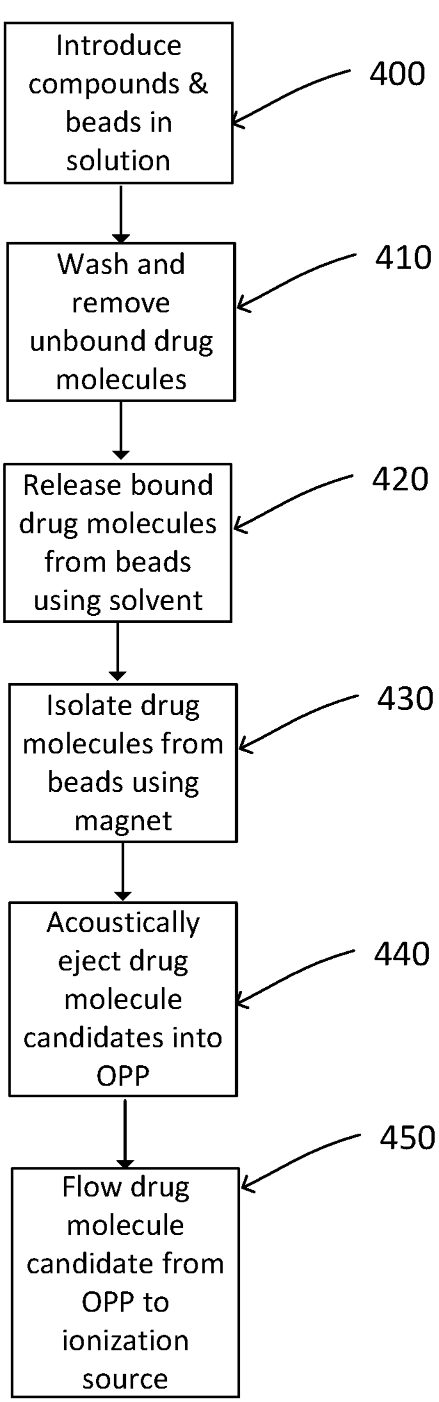
FIG. 4 depicts a method for identifying and separating compounds based on a selected affinity according to an embodiment.
Figure 5:
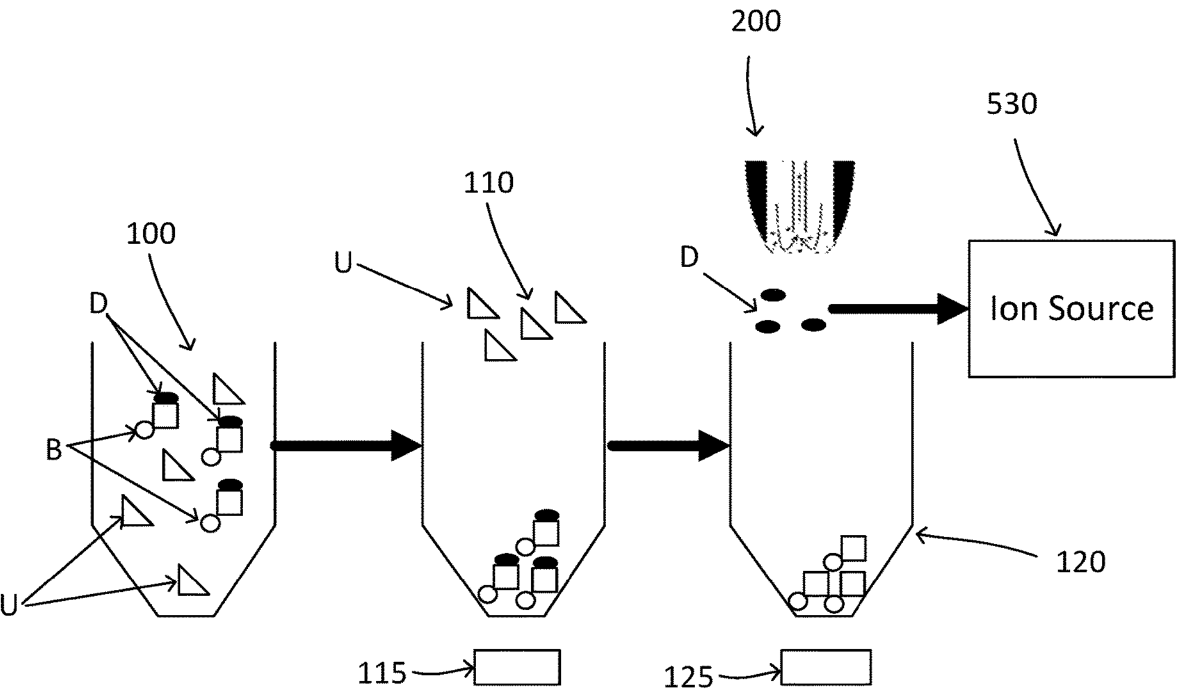
FIG. 5 depicts a possible system for implementing the method of FIG. 4.

In an embodiment, a method is provided for identifying and separating compounds based on a selected affinity, as set forth in FIG. 4 with reference to the system shown in FIG. 5. At 400, a plurality of drug molecule candidates (U and D) and magnetic beads (B) in solution are introduced to sample vessel 100, for example using an electromagnetic sampling device or probe to which the beads are magnetically attached, such that drug molecule candidates with affinity (D) bind to the magnetic beads. At 410, the beads (B) and bound drug molecule candidates (D) are transferred from the sample vessel 100 to wash vessel 110, for example using the electromagnetic sampling device or probe, whereupon the unbound drug molecules (U) are removed via washing while the beads (B) and bound drug molecule candidates (D) are retained in the vessel via a magnetic field from magnet 115. At 420, the washed beads with bound drug molecule candidates are removed from the wash vessel and introduced into separation vessel 120, for example using the electromagnetic sampling device or probe, where the drug molecule candidates (D) are released from the beads using organic solvent. At 430, the drug molecule candidates (D) are isolated from the magnetic beads (B) via magnet 125. At 440, the drug molecule candidates (D) are acoustically ejected from separation vessel 120 into OPI 200. Within the OPI 200, capture fluid travels towards the tip end 215 through the annular space 220 between the two cylindrical members and then travels away from the tip end through the inner cylinder as depicted in the arrows in the figure defining the fluid path. The capture fluid effectively eliminates the need to clean the sample. At 450, the solvent and ejected drug candidates (D) flow from the tip end 215 to the MS ionization source 530. Optionally or, if necessary, the drug molecule candidate (D) can be separated from the unbound drug molecules (U) using differential mobility spectrometry (DMS) or MS techniques (e.g. fragmentation patterns in MS-MS, etc.)

Figure 6:
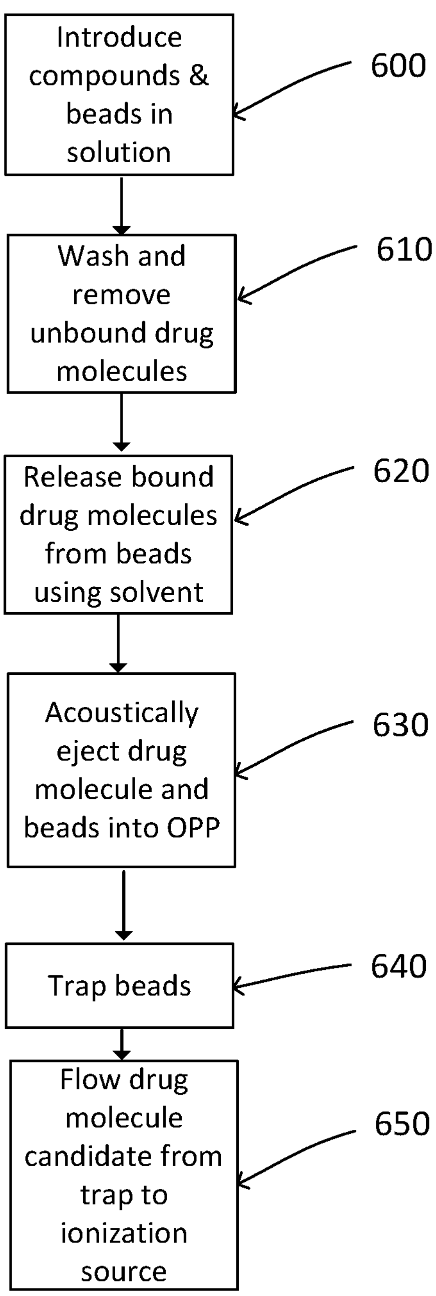
FIG. 6 depicts a method for identifying and separating compounds based on a selected affinity according to a further embodiment.
Figure 7:
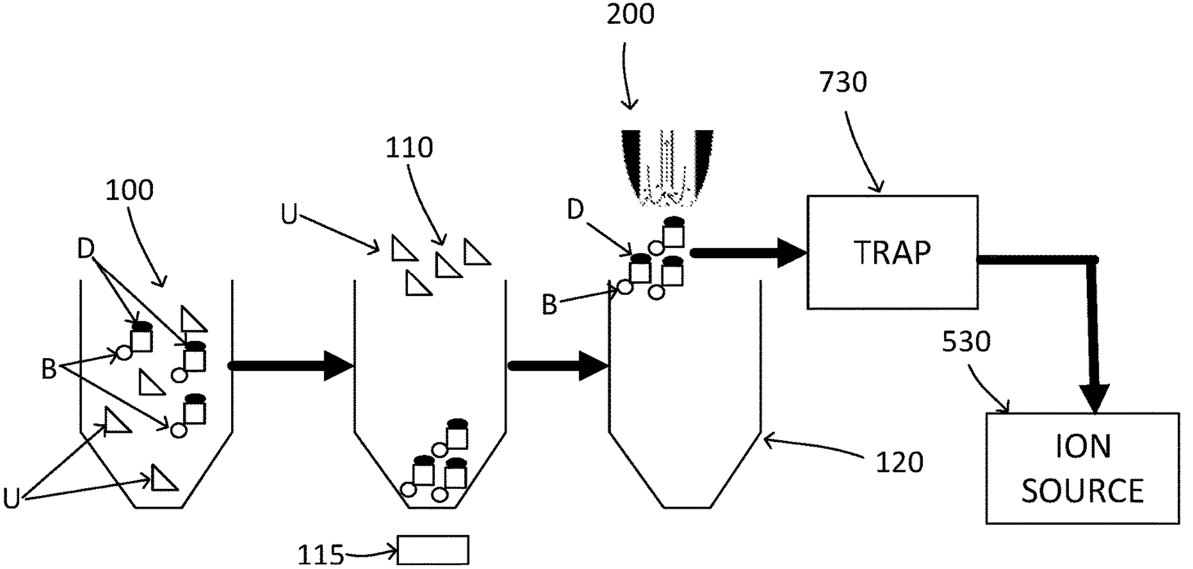
FIG. 7 depicts a possible system for implementing the method of FIG. 6.

In a further embodiment, a method is provided for identifying and separating compounds based on a selected affinity, as set forth in FIG. 6 with reference to the system shown in FIG. 7. At 600, a plurality of drug molecule candidates (U and D) and magnetic beads (B) in solution are introduced to sample vessel 100, for example using an electromagnetic sampling device or probe to which the beads are magnetically attached, such that drug molecule candidates with affinity (D) bind to the magnetic beads. At 610, the beads (B) and bound drug molecule candidates (D) are transferred from the sample vessel 100 to wash vessel 110, for example using the electromagnetic sampling device or probe, whereupon the unbound drug molecules (U) are removed via washing while the beads (B) and bound drug molecule candidates (D) are retained in the vessel via a magnetic field from magnet 115. At 620, the washed beads with bound drug molecule candidates are removed from the wash vessel and introduced into separation vessel 120, for example using the electromagnetic sampling device or probe, where the drug molecule candidates (D) are released from the beads using organic solvent. At 630, the drug molecule candidates (D) and beads (B) are acoustically ejected from separation vessel 120 into OPI 200. Within the OPI 200, capture fluid travels towards the tip end 215 through the annular space 220 between the two cylindrical members and then travels away from the tip end through the inner cylinder as depicted in the arrows in the figure defining the fluid path. The capture fluid effectively eliminates the need to clean the sample. At 640, the solvent, beads (B) and drug candidates (D) flow from the tip end 215 to an in-line trap 730 where the beads (B) are trapped (640). At 650, the solvent and ejected drug candidates (D) flow from the trap 730 to the MS ionization source 530. Alternatively, rather than separating the drug molecule candidates (D) from the beads in separation vessel 120, the drug molecule candidates (D) may be separated from the beads within OPI 200, where the capture fluid is a solvent.

Optionally or, if necessary, the drug molecule candidate (D) can be separated from the unbound drug molecules (U) using differential mobility spectrometry (DMS) or MS techniques (e.g. fragmentation patterns in MS-MS, etc.)

For acoustic ejection at 630, it is preferable that the drug molecule candidates (D) be uniformly suspended in the sample solution within separation vessel 120, for example by mechanically agitating the separation vessel 120 before dispensing or by integrating an electromagnetic mixer within the acoustic dispensing system.

Figure 8:
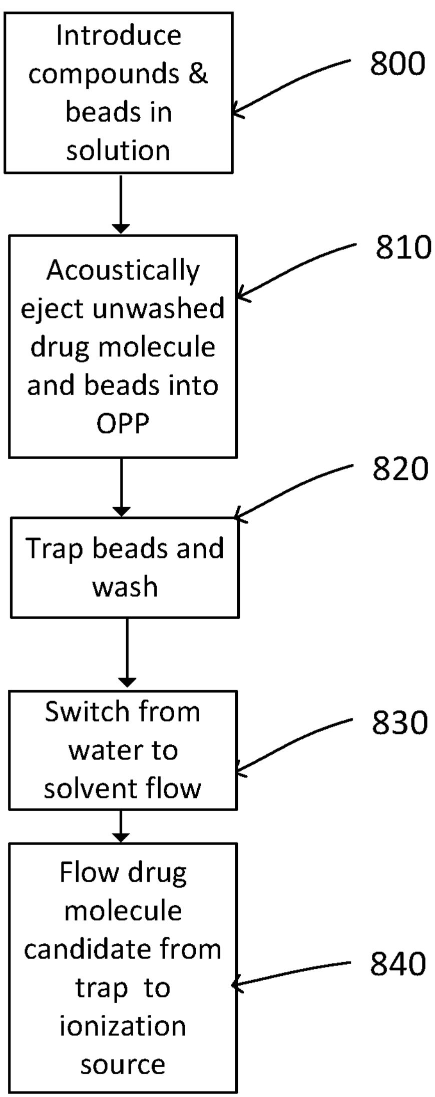
FIG. 8 depicts a method for identifying and separating compounds based on a selected affinity according to an additional embodiment.
Figure 9:
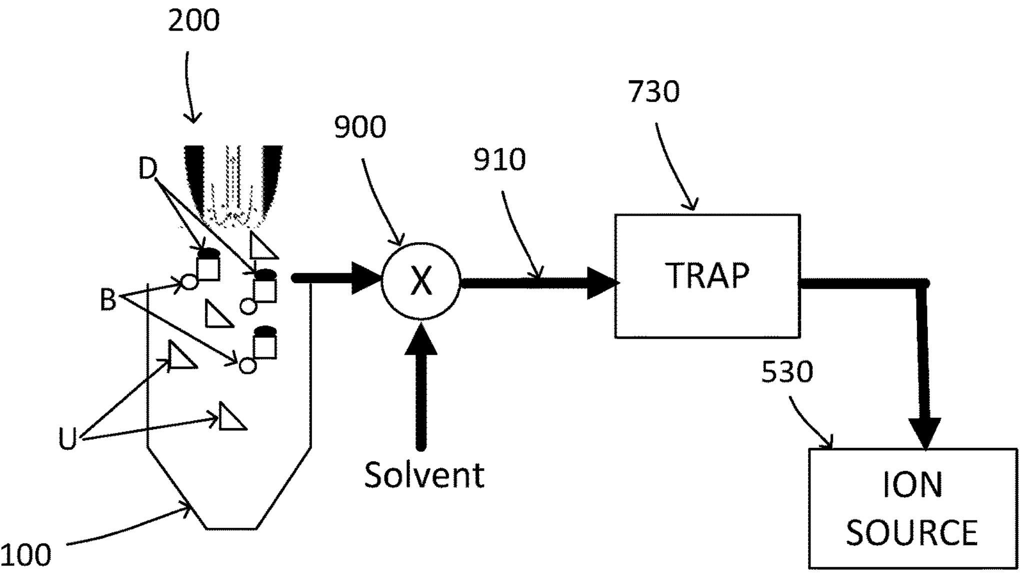
FIG. 9 depicts a possible system for implementing the method of FIG. 8.

In an additional embodiment, a method is provided for identifying and separating compounds based on a selected affinity, as set forth in FIG. 8 with reference to the system shown in FIG. 9. At 800, a plurality of drug molecule candidates (U and D) and magnetic beads (B) in solution are introduced to sample vessel 100, for example using an electromagnetic sampling device or probe to which the beads are magnetically attached, such that drug molecule candidates with affinity (D) bind to the magnetic beads. At 810, the unwashed drug molecule candidates (D) and beads (B) are acoustically ejected from sample vessel 100 into OPI 200. Within the OPI 200, capture fluid travels towards the tip end 215 through the annular space 220 between the two cylindrical members and then travels away from the tip end through the inner cylinder as depicted in the arrows in the figure defining the fluid path. The capture fluid (e.g. water) effectively eliminates the need to clean the sample. At 820, the solvent, beads (B) and unwashed drug candidates (D) flow from the tip end 215 to an in-line trap 730 where the beads (B) are trapped (640) and the drug candidates (D) are washed to remove unbound drug molecules (U). At 830, the flow of capture fluid (water) is switched to organic solvent flow via a valve 900 to separate the drug molecule candidates (D) from the beads (B). At 840, the solvent and selected drug candidates (D) flow via transport line 910 from the trap 730 to the MS ionization source 530.

Optionally or, if necessary, the drug molecule candidate (D) can be separated from the unbound drug molecules (U) using differential mobility spectrometry (DMS) or MS techniques (e.g. fragmentation patterns in MS-MS, etc.)

Figure 10:
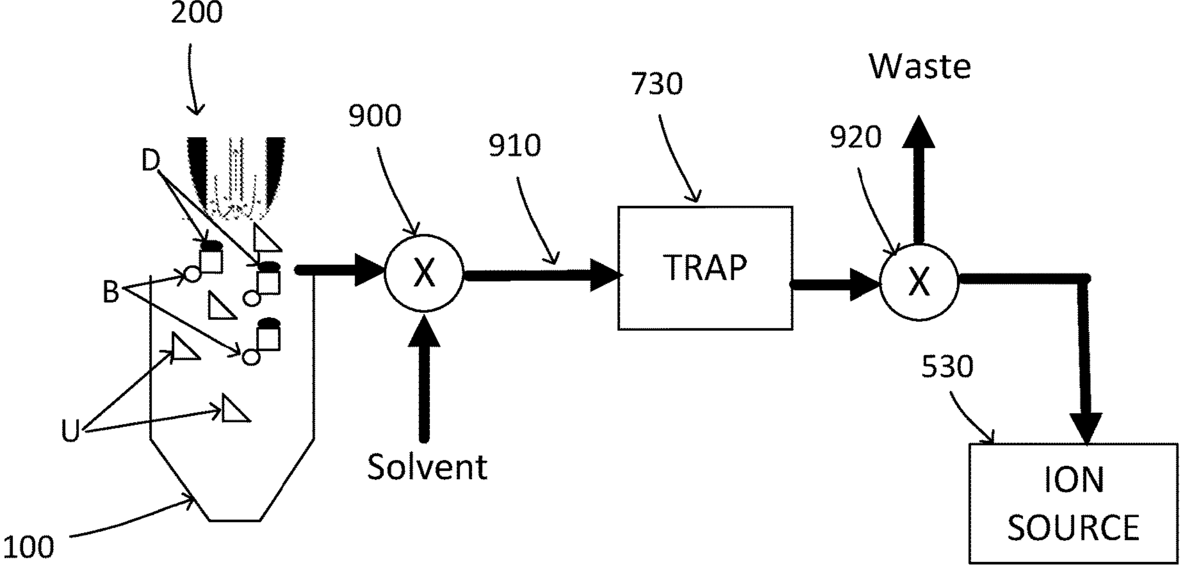
FIG. 10 depicts a possible variation of the system of FIG. 9.

Different embodiments of trap 730 are contemplated, including filters or size traps, or a permanent magnet that can be replaced from time to time, or an electromagnet that can be energized to trap magnetic beads (B) and then de-energized, for example during a cleaning cycle, to release any captured magnetic beads. As shown in FIG. 10, the transfer line 900 may include valve(s) 920 to redirect the flow of capture fluid to a waste vessel and thereby avoid releasing magnetic beads into the ionization source 530 during the cleaning cycle, when the electromagnet is de-energized to release captured beads.

In the system of FIG. 7, the trap 730 may be a magnetic trap at the tip end 215 of OPI 200 (i.e. electromagnets surrounding one or both of the first cylindrical member 205 and/or second cylindrical member 210, and wherein a clearing cycle may be performed with a solvent-based capture fluid to release the beads from the trap after the washed drug candidates have been conveyed to the MS ionization source 530.

In another embodiment, the trap 730 may be disposed at the ionization source 530 wherein bead trajectory separates from ions at entrance to the MS ionization source 530 due to the beads being much heavier than the ions, for use with the systems shown in FIGS. 5 and 9.

In a further embodiment, the trap 730 may an in-line magnetic trap on transport line 900 of the system shown in FIG. 9. It is contemplated that the in-line magnetic trap may be a replaceable section of transport line 900 that has a sufficient magnetic field to capture the magnetic beads (B) within the transport line.

It is also contemplated that in the system of FIG. 5, employing acoustic ejection of drug molecule candidates (D) isolated from the beads (B), a permanent magnet guard trap may be included to protect the ionization source 530 and MS form unintentional ejection of magnetic beads from the vessel 120.

Although the systems depicted in FIGS. 5 and 7 discuss the use of separate sample, wash and separation vessels 100, 110 and 120, it is contemplated that sample preparation may be performed in a single vessel or multiple vessels.

In each of the embodiments set forth in FIGS. 4-10, as an alternative to introducing the compounds drug molecules with affinity to the solid phase surfaces of the magnetic particles (B), it is contemplated that the particles (B) can be added after the protein-drug integration in free solution (e.g. after 400, 600, 800), and used to fish-out the protein-drug complex rather than the protein pre-immobilized on magnetic particles (B).

The many features and advantages of the invention are apparent from the detailed specification and, thus, it is intended by the appended claims to cover all such features and advantages of the invention that fall within the scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method for identifying and separating compounds based on a selected binding affinity for a selected protein comprising:

introducing a plurality of compounds together in a solution in a sample vessel;

inserting a probe into the sample vessel, wherein the probe comprises a surface treatment, and the surface treatment binds with one or more compounds based on the selected binding affinity of the one or more compounds for a selected protein;

binding one or more compounds from the plurality of compounds to the probe;

removing the probe and bound one or more compounds from the solution in the sample vessel;

separating the one or more compounds from the probe after removal of the probe from the sample vessel;

capturing the separated one or more compounds with flowing solvent at an open end of an open port sampling interface;

transporting the solvent and captured one or more compounds to an ionization device; and, ionizing the one or more compounds.

2. The method of claim 1 further comprising:

analyzing the ionized one or more compounds in a mass spectrometer.

3. The method of claim 2, wherein after ionizing the one or more compounds but before the analyzing, the method further comprises:

separating the ionized one or more compounds based on ion mobility in a differential mobility spectrometer.

4. The method of claim 1, wherein the probe is selected from the group consisting of:

a Solid Phase Micro Extraction (SPME) fiber;

a REED; and a magnetic particle.

5. The method of claim 1, wherein the separating the one or more compounds from the probe comprises: injecting the unbinding solvent and unbound one or more compounds into the flowing solvent at the open end of the open port sampling interface.

6. The method of claim 5, wherein the injecting comprises:

aspirating the unbinding solvent and unbound one or more compounds from the separation vessel; and injecting the aspirated unbinding solvent and unbound one or more compounds into a solvent stream pumped to the ionization device.

7. The method of claim 5, wherein the injecting comprises ejecting droplets of the unbinding solvent and unbound one or more compounds from the separation vessel into the flowing solvent at the open end of the open port sampling interface.

8. The method of claim 7 wherein the injecting comprises acoustically or pneumatically ejecting the droplets.

9. In a system for affinity selection by mass spectrometry, wherein a plurality of drug candidates in solution are separated based on binding affinity, a method comprising:

introducing a solid-phase device having binding affinity for a selected protein into the solution in a sample vessel, wherein the solid-phase device comprises a surface treatment, and the surface treatment binds with at least one of the plurality of drug candidates to the solid-phase device based on the selected binding affinity of the at least one of the plurality of drug candidates, thus acting as a selected drug candidate;

binding at least one of the plurality of drug candidates to the solid-phase device as a selected drug candidate;

washing the solid-phase device and selected drug candidate to separate unbound material after removal of the solid-phase device from the sample vessel;

sampling the selected drug candidate in capture fluid flowing through a sampling region of an open port sampling interface and directing the sampled selected drug candidate and capture fluid to an ionization source.

10. The method of claim 9, wherein the solid-phase device is selected from the group consisting of a solid phase microextraction fiber, a REED and a magnetic particle.

11. The method of claim 9, wherein said protein is immobilized to a surface of the solid-phase device by treating Si—OH on the surface with aminosilane reagents followed by reaction with glutaraldehyde (GA), the free-end of GA being capable of reacting with the amino groups of lysine to capture the protein.

12. The method of claim 9, wherein the selected drug candidate is sampled by acoustically ejecting the selected drug candidate from a sample well into the capture fluid.

13. The method of claim 12, wherein the selected drug candidate is ejected from the sample well after the washing.

14. The method of claim 12, wherein before the selected drug candidate is ejected from the sample well the method further comprises:

releasing the selected drug candidate from the solid-phase device;

isolating the selected drug candidate from the solid-phase device; and ejecting the selected drug candidate without the solid-phase device into the capture fluid.

15. The method of claim 12, wherein the selected drug candidate is ejected in a bound state with the solid-phase device.

16. The method of claim 15, wherein the selected drug candidate is unbound by the capture fluid.

17. The method of claim 12, wherein the selected drug candidate and solid-phase device are ejected from the sample well, and wherein the system further comprises a trap for trapping the solid-phase device before the ionization source.

18. The method of claim 17, wherein the candidate drug is released from the trapped solid-phase device by introducing solvent into the capture fluid.

19. The method of claim 17, wherein the trap comprises a magnetic trap.

20. The method of claim 17, wherein the trap comprises a filter or size trap.

* * * * *